US010159622B2

(12) United States Patent
Dills

(10) Patent No.: US 10,159,622 B2
(45) Date of Patent: Dec. 25, 2018

(54) VIBRATOR

(71) Applicant: AMOR Gummiwaren GmbH, Arndstadt (DE)

(72) Inventor: Michael Dills, Arnstadt (DE)

(73) Assignee: Amor Gummiwaren GmbH (DE)

( * ) Notice: Subject to any disclaimer, the term of this patent is extended or adjusted under 35 U.S.C. 154(b) by 85 days.

(21) Appl. No.: 15/319,907

(22) PCT Filed: Jul. 9, 2015

(86) PCT No.: PCT/EP2015/065722
§ 371 (c)(1),
(2) Date: Dec. 19, 2016

(87) PCT Pub. No.: WO2016/005507
PCT Pub. Date: Jan. 14, 2016

(65) Prior Publication Data
US 2017/0119619 A1 May 4, 2017

(30) Foreign Application Priority Data
Jul. 11, 2014 (EP) .................................... 14176777

(51) Int. Cl.
*A61F 5/00* (2006.01)
*A61H 19/00* (2006.01)
*A61H 23/02* (2006.01)

(52) U.S. Cl.
CPC ............. *A61H 19/30* (2013.01); *A61H 19/34* (2013.01); *A61H 23/0263* (2013.01); *A61H 2201/1215* (2013.01); *A61H 2201/165* (2013.01); *A61H 2201/1645* (2013.01); *A61H 2201/501* (2013.01); *A61H 2201/5015* (2013.01); *A61H 2201/5097* (2013.01)

(58) Field of Classification Search
CPC ......... A61H 19/30; A61H 19/34; A61H 23/00
USPC ......................................... 600/38–41; 601/46
See application file for complete search history.

(56) References Cited

U.S. PATENT DOCUMENTS

| | | | | |
|---|---|---|---|---|
| 9,050,240 | B2 * | 6/2015 | Howsam ................ | A61H 19/44 |
| 2003/0181784 | A1 | 9/2003 | Klein | |
| 2006/0082441 | A1 | 4/2006 | Papamihalis | |
| 2008/0009775 | A1 * | 1/2008 | Murison ................ | A61H 19/34 601/46 |
| 2015/0335520 | A1 * | 11/2015 | Dills ...................... | A61H 19/44 601/46 |

FOREIGN PATENT DOCUMENTS

DE 202009008573 U1 11/2010

* cited by examiner

*Primary Examiner* — John Lacyk

(57) ABSTRACT

A vibrator including a curved housing adapted to the female anatomy, the housing has a front section; a rear section; an interior section and a fastening section. The interior section has a power source, a control unit, a memory unit for saving data, a communication unit for data communication with an external device and an electric motor for generation of a vibration. The rear section is configured to transmit vibrations generated by the electric motor to the body. Fasteners are included for fastening the vibrator to an article of clothing by a clamping mechanism. The fasteners are removably attached to the fastening section of the housing and are flush with the front section.

12 Claims, 4 Drawing Sheets

VIBRATOR

FIELD OF THE INVENTION

The present invention pertains to a vibrator, and more particularly, a vibrator adapted for wireless data communication exchange.

BACKGROUND OF THE INVENTION

Vibrators are erotic toys which serve the purpose of sexual stimulation and massage, and they can also have human medical applications. To this end, the vibrator generates vibrations or, in more general terms, oscillations and/or movements, which are usually produced by an electric motor with an off-center weight. In order to stimulate a person using the vibrator, the vibrator is brought into contact with especially sensitive body parts such as the external or internal sex organs.

Vibrators which are placed on sensitive body parts are adapted in particular to the anatomy of the female body. The body parts in question are stimulated by the vibrations generated by the vibrator.

A vibrator of this type is described in, for example, GB 2 479 735 A and comprises a flat, essentially triangular shape. The known vibrator also comprises a display field and a control pad on the outside surface of its housing to facilitate the activation of its functions. The vibration is generated by an electric motor, which rotates an off-center weight on its drive shaft. The power is supplied by a battery, preferably rechargeable, located in the housing. The disadvantage of this known vibrator is that it is controlled by way of the outward-facing control pad; this is disadvantageous because of the inconvenience attendant on the need to remove the vibrator from its position on the body when the user wishes to change from one function to another. In addition, there is no way to anchor the vibrator in its functional position.

The erotics industry makes most of its sales today over the Internet, especially by providing photographs and videos against payment of a fee. To an increasing extent, interaction between the customer and the service provider is also becoming more widespread, such as that made possible by the use of application programs ("apps") to communicate via web cams or smartphones, wherein the customer receives video and audio signals from a service provide over the Internet in real time. With the further development of the technical possibilities, there is a search for new modes of communication and interaction between customer and service provider over the Internet medium. The use of a vibrator by the service providers is a popular variant.

In the age of global data exchange on social networks, furthermore, the sharing of data has greatly increased. To an equal extent the technical possibilities for controlling electrical devices of all types through the use of application programs, so-called "apps", which are available for smartphones, tablet computers, and other mobile computing devices, are also increasing.

It is therefore the object of the present invention to provide a vibrator of simple structure and small dimensions, which can be produced at low cost, is adapted to wireless data communications exchange and can thus be operated wirelessly, and can be easily anchored in its functional position.

SUMMARY OF THE INVENTION

According to the invention, a vibrator is provided having a curved housing adapted to the female anatomy; the housing comprising a front section and a rear section, and in the interior, the vibrator having a power source, a control unit, a memory unit, a communications unit, and an electric motor, wherein the rear section is adapted for the transmission of vibrations from the vibrator to the body, and wherein fastening means for fastening the vibrator to an article of clothing are provided, the fastening means being removably attached to a fastening section of the housing and being flush with the front section. The simple structure and design of the vibrator makes it possible for the dimensions to be kept so small that, for example, it has very little bulk and is not perceived to be interfering. Because of its flat, slightly curved, anatomically adapted shape, the vibrator can be worn comfortably and can hardly be identified from the outside. The way in which it is fastened to, for example, the user's underclothing is secure and simple through the use of a clamping mechanism, as a result of which the unit can be worn comfortably and is easily handled.

It is advantageous for the fastening means to be preferably magnetically configured. It is highly preferable that the fastening means comprise a fastening plate of magnetic material and at least one magnet arranged on the fastening sections. The fastening plate is made of ferromagnetic material, e.g., a high-grade ferritic steel, and the magnets are, for example, neodymium magnets made of neodymium-iron-boron alloy or comparable material. Instead of the magnetic fastening means, it would also be possible as an alternative to use some other type of clamping mechanism such as interlocking snaps, which are designed to clamp a layer of clothing between the opposing elements. Several of these interlocking elements can also be provided to ensure a sufficiently secure attachment of the fastening plate to the housing, but they are nevertheless capable of being disconnected easily.

Preferably, the rear section comprises a projection which is configured as a vibratory part for stimulating parts of the body. Thus, the rear section can be shaped to adapt it to the effective transmission of vibrations to the sensitive body parts such as the clitoral region. It is also conceivable that several projections could be provided, each of which is equipped with its own vibratory motor, so that the motors can be actuated either separately from each other or as a unit.

The surfaces at the transition from the front section of the housing to the fastening means are preferably essentially smooth. Thus, the device can be worn comfortably, because, when the vibrator according to the invention is being worn, no edges, corners, or the like which could produce unpleasant sensations are present in the sensitive body regions.

It is also preferable for the housing to comprise a head part, wherein the transition between the head part and the rear section is formed by a flexible section. It is advantageous for it to be possible to fold or flip the head part around the flexible section, which serves as the axis of a hinge, by essentially 180°.

The housing preferably comprises a connecting element, which is adapted for charging of the power source. The connecting element is preferably configured as a USB type A plug, which is designed to plug into a USB type A port and thus make an electrical connection.

After the head part has been flipped over by 180° and the fastening plate has been removed, the connecting element of the housing is then preferably exposed. Thus a simple mechanism for exposing the connection for charging the energy storage unit, i.e., the battery, of the vibrator is created. For this purpose, it is necessary simply to remove the fastening plate and then to fold or flip the head part back.

Except for the fastening plate itself there are no separate parts which could be lost by the user.

It is especially preferable for the external elements of the housing, with the exception of the fastening plate, to comprise silicone material. Silicone material is medically safe, easy to clean, and neutral to the skin. It is also easy to manufacture, widely used in the industry and is also low in cost.

The communications unit preferably comprises a Bluetooth® module, which is adapted to wireless communication in both directions. Thus, the possibility of remote control is created such as control from a smartphone, tablet computer, a PC, or the like. This also enables the vibrator to be controlled over the Internet, i.e., by a remote computer or smartphone. This offers new possibilities for the use of the vibrator according to the invention.

It is also advantageous for the vibrator to comprise a plurality of preferably miniaturized vibratory motors, which are adapted to transmit vibrations from the vibrator to the body.

The vibrator according to the invention can be remotely controlled wirelessly and, through the use of miniaturized components, also has a long battery life and the vibratory effect is nevertheless sufficient to bring about a corresponding positive effect on the user.

The fastening or anchoring function prevents unintentional displacement or separation of the vibrator from its ideal position on an article of clothing lying directly on the body. At the same time, the user can detach the vibrator from the article of clothing, such as from the underwear, with a few manual operations and move it elsewhere or remove it completely. The fastening plate is attached to the forward or outside surface of the vibrator and is flush with it, so that there are no troublesome transitions such as edges or the like. The user friendliness is thus improved even more.

The vibrator also lacks any kind of control pads or operating elements, which additionally simplifies its use and improves handling, because the device is operated exclusively from a remote location. As soon as the vibrator is in its intended position, the user can assume a relaxed, comfortable position and turn on and control the vibrator functions from a smartphone, for example. Through the exchange of data between the smartphone and the Internet, it is also possible that a second person could control the vibrator remotely. This opens up a large number of new possibilities for the use of the device.

The charging plug of the vibrator, furthermore, can be exposed in such a way that it can be connected to almost any USB port to recharge the battery. In addition, one could also provide other contacts on the USB plug of the vibrator so that data can be supplied to, for example, a memory unit or a central processing unit or so that data can be transmitted from such units.

BRIEF DESCRIPTION OF THE DRAWINGS

The invention is explained in greater detail below with reference to the embodiments illustrated in the drawings.

DETAILED DESCRIPTION

Figure 1:
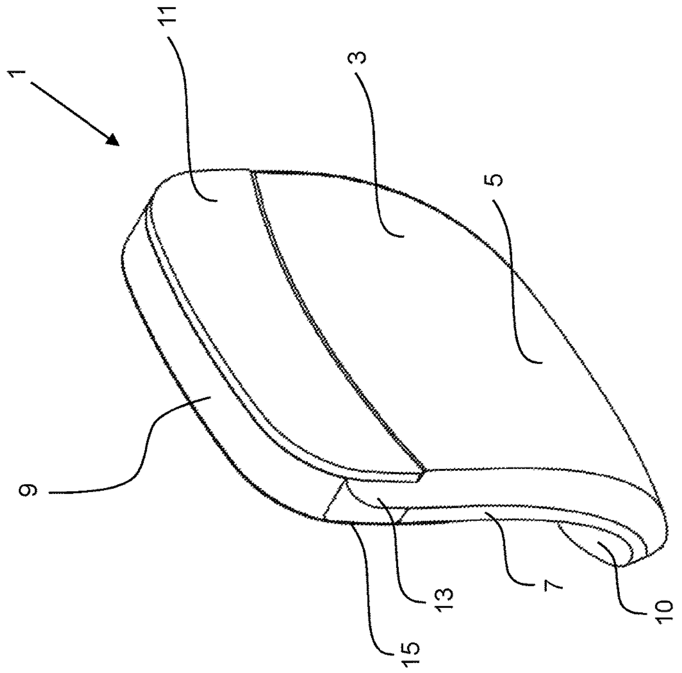
FIG. 1 is a perspective view of a preferred embodiment of the vibrator according to the invention.

FIGS. 1-12 illustrate a preferred embodiment of a vibrator. FIG. 1 shows a perspective view, from above, of a preferred embodiment of the vibrator 1 according to the invention, wherein the vibrator is tilted slightly forward and to the side. Vibrator 1 comprises a smooth, slightly curved housing 3 with a front section 5, a rear section 7, and, in the upper area, a fastening plate 11. Fastening plate 11 is arranged on the front of housing 3 on a head part 9 and is flush with front section 5. Fastening plate 11 in this embodiment is detachably connected to a fastening section 13 of the housing by magnetic fastening means. Alternatively, other, nonmagnetic fastening means with a clamping mechanism are also possible such as snaps or other latching type connecting means. Approximately at the level of fastening section 13, there is, on the rear of housing 3, a flexible section 15, the function of which will be explained in detail further below. In the lower area of vibrator 1, rear section 7 comprises a projection 10, which is adapted to transmit vibrations from the vibrator to the body, especially to the clitoral region.

Figure 2:
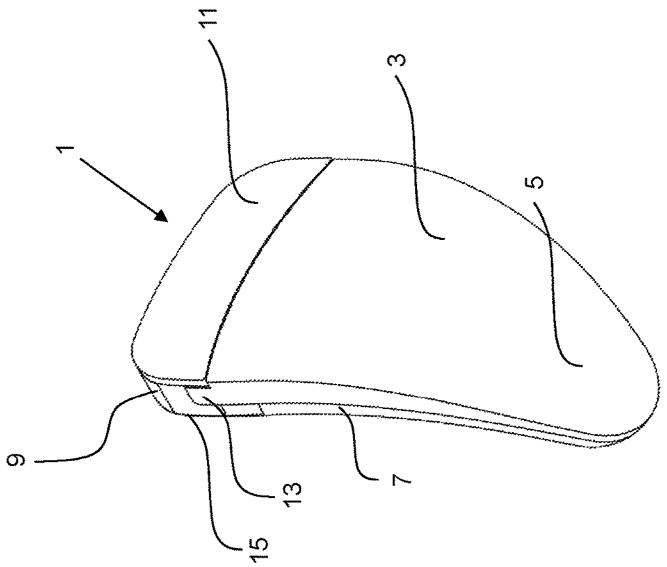
FIG. 2 is a perspective view of the preferred exemplary embodiment of the vibrator according to the invention of FIG. 1.

FIG. 2 shows a perspective view of the preferred embodiment of vibrator 1, similar to the view of FIG. 1 but from further below. For the sake of simplicity, the description of the elements will not be repeated. It can be seen in FIG. 2 that the surface transition between front section 5 of housing 3 and fastening plate 11 is essentially smooth, i.e., without projections or edges.

Figure 3:
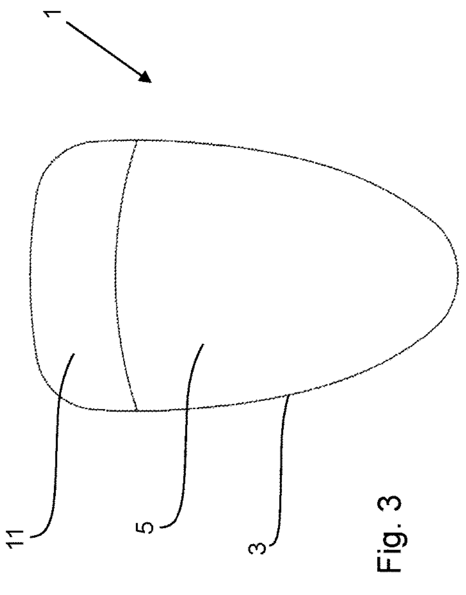
FIG. 3 is a front view of the vibrator of FIG. 1.
Figure 4:
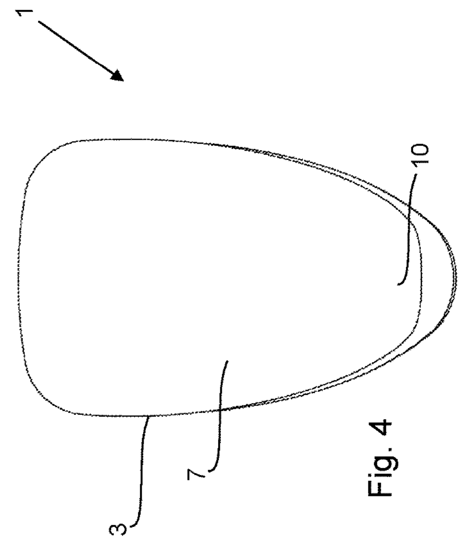
FIG. 4 is a rear view of the vibrator of FIG. 1.
Figure 5:
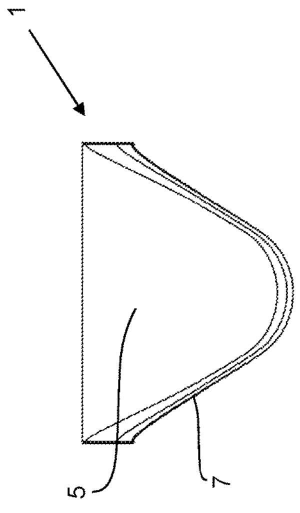
FIG. 5 is a view from below of the vibrator of FIG. 1.
Figure 6:
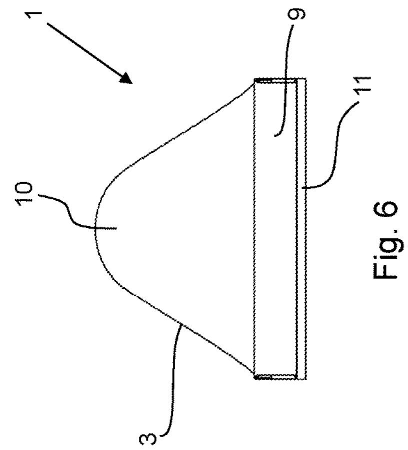
FIG. 6 is a view from above of the vibrator of FIG. 1.

FIG. 3 shows a front view of the preferred embodiment of vibrator 1. FIG. 4 shows a rear view of the preferred embodiment of vibrator 1 wherein projection 10, which amounts essentially to the vibratory part, is arranged in the lower area of front section 7 of housing 3. FIG. 5 shows a view from below onto vibrator 1 according to the invention, and FIG. 6 shows a view from above of the preferred embodiment of vibrator 1. In FIGS. 3 and 5, the primary surface which can be seen is the front section, whereas, in FIGS. 4 and 6, it is the rear section which can be seen. Fastening plate 11, which rests directly on head part 9, can also be seen clearly in FIG. 6. It can be derived from FIGS. 3 to 6 that the vibrator comprises rounded, smooth surfaces without any sharp edges.

Silicone, e.g., RTV silicone, is the preferred material for housing 3 and the external elements of vibrator 1. Other thermoplastic elastomers with properties similar to those of silicone can also be used.

Figure 7:
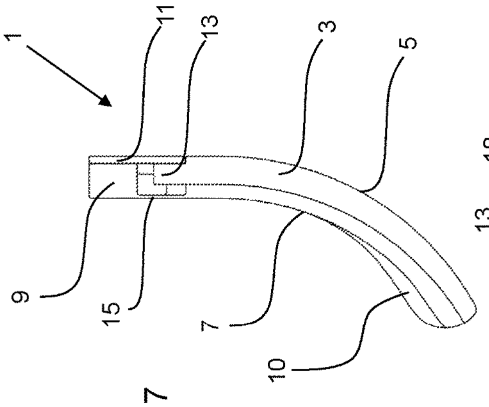
FIG. 7 is a side view of the vibrator of FIG. 1 in a first position.

FIG. 7 shows a side view of the preferred embodiment of vibrator 1. In the lower area, projection 10 on rear section 7 of housing 3 is clearly identifiable. The elevation of projection 10 from the surrounding surface is, for example, in the approximate range of 1 mm to 5 mm in thickness, and its surface dimension, i.e., its length, is in the approximate range of 10 mm to 30 mm. These values are only orientational, however; it is therefore also possible to select dimensions larger than or smaller than these ranges for projection 10, depending on the size and material of the vibrator.

It can also be seen in FIG. 7 that the lower area of fastening plate 11 rests flat on fastening section 13, and its upper area rests flat on head part 9. How fastening plate 11 is attached in the preferred embodiment of vibrator 1 according to the invention will be described in greater detail below with reference to FIGS. 9 to 11. The transition between head part 9 and rear section 7 in the preferred embodiment is formed by flexible section 15, which assumes the function of a type of hinge, as will be explained below with reference to FIGS. 8 to 10.

Figure 8:
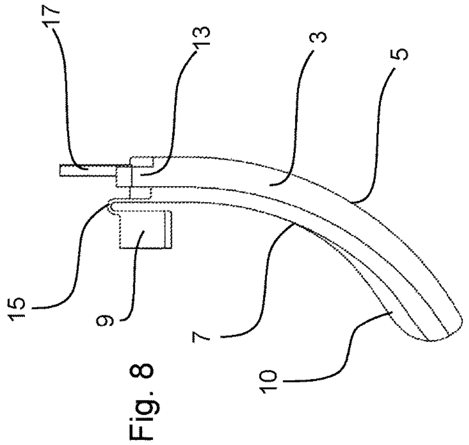
FIG. 8 is a side view of the vibrator of FIG. 1 in a second position.

In the side view shown in FIG. 8, which is derived from FIG. 7, one can see the preferred embodiment of vibrator 1 according to the invention in a second position, in which fastening plate 11 has been removed and head part 9 has been flipped open. The second position shown in FIG. 8 represents the state in which vibrator 1 is arranged when it is to be connected to a power source or energy supply by way of connecting element 17, which is located in the upper area, for the purpose of charging the battery. In the embodiment shown, connecting element 17 is configured in the form of a USB type A plug, which can be inserted into any standard commercial USB type A port. After fastening plate 11 (see FIG. 7) has been removed, connecting element 17 is essentially freely exposed on the front of vibrator 1, but it is still covered from above and from behind by head part 9. In the embodiment shown here, head part 9 is connected to rear section 7 by a flexible section 15 approximately at the level of fastening section 13 of housing 3. As a result of the flexible properties of the thin, flexible section 15, head part 9 can be folded or flipped back and down, thus completely exposing connecting element 17. In this position, shown in FIG. 8, connecting element 17 can, therefore, be connected to a corresponding mating part for the purpose of charging the battery of the vibrator.

Figure 9:
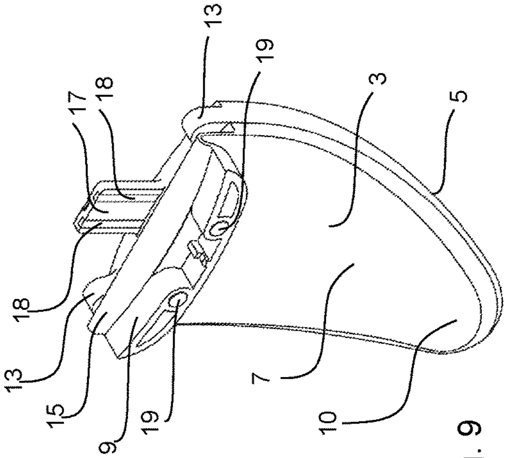
FIG. 9 is a perspective view of the vibrator of FIG. 1 from the back in the second position.

The state of the second position shown in FIG. 8 is shown again in FIG. 9 in a perspective view. It can be seen that head part 9 has been flipped back and down by essentially 180°, thus completely exposing connecting element 17. It can also be seen that flexible section 15 extends over the entire width of vibrator 1. Because all of the external housing components are made of silicone, it is obvious that, if flexible section 15 is configured with a wall of appropriate thinness, its bending properties will be obtained automatically.

Parts of the fastening device responsible for the attachment of fastening plate 11 to head part 9 can also be seen in FIG. 9. In recesses provided for the purpose, magnets 19 are inserted or pressed into head part 9; these magnets, in the preferred embodiment, are configured as standard commercial neodymium magnets. Neodymium magnets of neodymium-iron-boron alloy have a very strong magnetic field strength and high remanence, for which reason they are extremely well adapted to the purpose of holding (ferro) magnetic fastening plate 11 in place.

Figure 10:
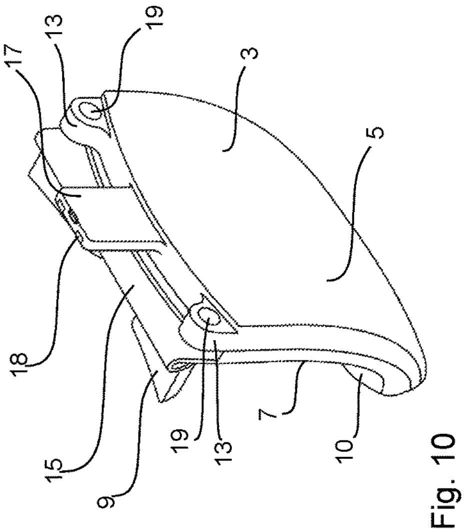
FIG. 10 is a perspective view of the vibrator of FIG. 1 from the front in the second position.

In FIG. 10, which shows a perspective view of the preferred embodiment of the vibrator in the second position in analogy to FIG. 9, although in a view from the front, it can be seen similarly that the upper section of housing 3 comprises a fastening section 13 on each of its outer sides; a magnet 19 is also pressed into a corresponding recess in each of these sections. These magnets therefore face toward the front. Magnets 19 in head part 9 are visible in FIG. 9, these magnets serve to hold fastening plate 11 in its proper position.

Figure 11:
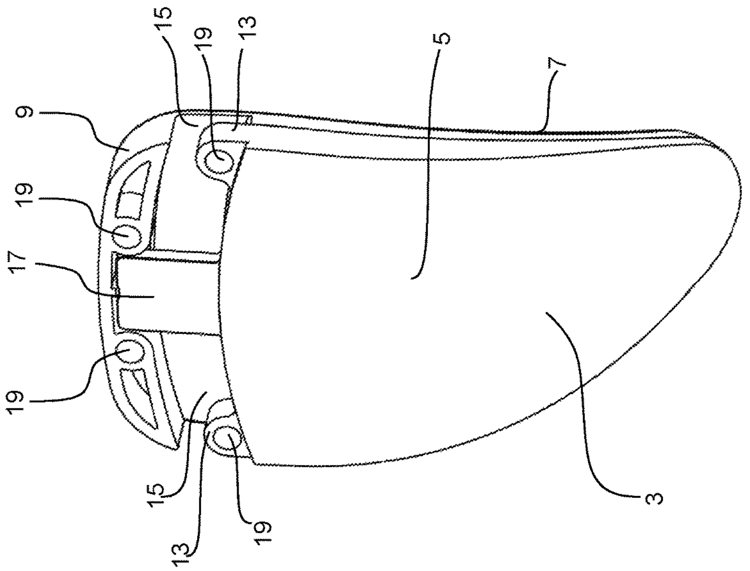
FIG. 11 is a perspective front view of the vibrator of FIG. 1 with the fastening plate removed.

FIG. 11 shows the preferred embodiment of vibrator 1 in the position before fastening plate 11 is set into position and held in its proper position by magnets 19. As can also be seen in FIG. 10, fastening plate 11 is set onto an essentially transverse edge, so that it is flush with the front section of housing 3. On its rear surface, fastening plate 11 is flush with connecting element 17, wherein contact elements 18 (not visible in FIG. 11) are arranged on the rear surface or back of connecting element 17. Head part 9, in contrast to what is shown in FIGS. 8-10, has now been flipped into its normal position, wherein it protectively encloses the upper area of connecting element 17. Magnets 19 of head part 9 in the embodiment shown here are arranged directly to the right and to the left of connecting element 17, so that a total of four magnets 19 are obtained for holding fastening plate 11 in position. As a result of the position of magnets 19 near connecting element 17, the cover provided by head part 9 protects connecting element 17 in an especially effective manner. It is obvious that fewer than four or more than four magnetic elements could also be arranged on head part 9 or also on other sections of housing 3 to hold fastening plate 11 in place. The material of fastening plate 11 is preferably a ferritic high-grade steel with a thickness of 1.5 mm, for example, which can comprise a brand name or logo on its front surface, i.e., the visible side.

From what has been said above it can be easily understood that the rear side of vibrator housing 3, i.e., rear section 7, including the rear wall of head part 9 with flexible section 15, results in a completely closed surface. This is especially important because this entire rear surface rests directly on the body of the user and for this reason should not have any edges, grooves, or other irregularities.

Figure 12:
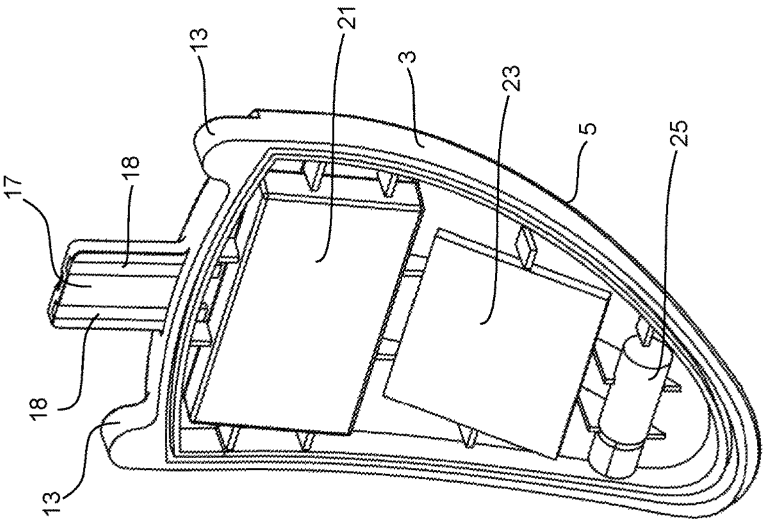
FIG. 12 is a perspective view of parts of the vibrator of FIG. 1.

FIG. 12 shows the "interior life" of the preferred embodiment of vibrator 1 according to the invention, wherein the rear section and fastening plate 11 are not shown in FIG. 12. In the upper area of the interior of housing 3 is the power source or energy storage unit 21, which is configured preferably as a lithium-ion or lithium-polymer battery with a capacity of 300 mAh. Underneath this is connected a printed circuit board or PCB 23, which comprises essentially all of the control, memory, and communications units in the form of electronic circuitry. In particular, the circuit board 23 comprises a central processing unit and a communications element configured as a Bluetooth® module, which is responsible for wireless communication in both directions. The Bluetooth® module is adapted to transmit all of the control functions of vibrator 1. This means that an additional memory element does not necessarily have to be present on circuit board 23. All of the elements are mounted in the housing by the use of webs, plates, recesses, and projections, which are preferably configured as integral parts of the housing. As a result, the electronic components and the electronic connecting elements (not shown) can be pressed permanently into the housing and thus held in place there.

In the lower part, electric motor 25 is arranged, which is configured as a vibratory motor with an off-center weight seated on its drive shaft. In the embodiment shown here, only a single vibratory motor 25 is shown in the interior of vibrator 1, but it is also possible, depending on the size of the motor and the amount of space available, to arrange more than one miniaturized vibratory motor 25 in vibrator 1. It can be seen that vibratory motor 25 is arranged in essentially the same area as that of projection 10 on rear section 7 of housing 3, which means that most of the vibration occurs in the area of projection 10. It is also conceivable that miniaturized vibratory motors could also be arranged in other sections of the rear surface of vibrator 1. A peripheral groove can also be seen FIG. 12, into which groove a correspondingly arranged projection on the rear section, configured as a separate housing part, can be inserted, so that a secure connection is obtained between the components.

In the preferred embodiment shown, the thickness of the vibrator over most of its extent is approximately 9 mm, and, in the lower section in the area of projection 10, it is about 12 mm. The overall width of the vibrator is approximately 52 mm, and the width in the lower section of projection 10 is approximately 20 mm. Other dimensions can also be selected for the design presented here, however; in particular, the thicknesses can be reduced even more, and the length and width of the vibrator can be made even smaller. This is important especially for the reason that, the smaller dimensions of the device, the more convenient it is for the user to carry it on the body. In addition, the vibrator should have as little bulk as possible and also be light enough to be carried around easily.

The advantageous fastening or fixation of vibrator 1 to a piece of fabric, preferably a woman's underclothing, is accomplished by first removing fastening plate 11 and then placing the vibrator on the body, e.g., in the vaginal area, in such a way that projection 10 of vibrator 1 is as close as possible to the sensitive body areas and can thus transmit the vibrations to those areas. After the positioning step, fastening plate 11 is placed on top of the section of the underclothing fabric located over the upper part of vibrator 1, so that magnets 19 on housing 3 or on head part 9 of vibrator 1 facing the inside surface of the underclothing (the surface of the fabric facing the body) attract metal fastening plate 11, as a result of which the lower edge of fastening plate 11 preferably engages with the upper edge of front section 5 of vibrator 1; the area of underclothing fabric lying between the vibrator and fastening plate 11 is thus firmly clamped. As a result, vibrator 1 is held securely in position at the desired point but can be easily shifted, repositioned, or removed by the user simply by removing (briefly) fastening plate 11 and, after vibrator 1 has been repositioned as desired, by setting plate 11 back into position again. This fastening solution requires no additional elements such as pockets or locking element and is therefore extremely simple and low in cost.

The vibrator according to the invention can be used in conjunction with many different types of underclothing such as thongs, slips, tangas, panties, bikinis, body stockings, or the like.

As an alternative to the embodiment described above, fastening plate 11 does not necessarily have to be arranged in the upper part of vibrator 1 but can instead carry out its function in the middle part. The retaining magnets on the housing can be made flat for this purpose. It is also possible to use more than one fastening plate 11 to improve the retaining function.

As an alternative, it is possible to use a fastening means different from the magnetic fastening system; for example, it is possible to use interlocking snaps, eyelets, or the like, which clamp the fabric of the underclothing with sufficient force and which can also be easily unsnapped again.

Vibrator 1 can also have a different basic outline; for example, it can be made in the form of a figure-eight, i.e., with a narrow waist part between a wide upper area and wide lower area.

The subject matter of the present invention provides a vibrator of simple structure with small dimensions, which can be produced at low cost, is adapted to wireless data exchange and can therefore be operated wirelessly, and can be easily held in place in its functional position.

A wide variety of materials are available for the various parts discussed and illustrated herein. While the principles of this device have been described in connection with specific embodiments, it should be understood clearly that these descriptions are made only by way of example and are not intended to limit the scope of the device.

The invention claimed is:

1. A vibrator comprising:

a curved housing adapted to the female anatomy, the housing including:
- a front section;
- a rear section;
- an interior section, the interior section of the housing having a power source, a control unit, a memory unit for saving data, a communication unit for data communication with an external device and an electric motor for generation of a vibration; and
- a fastening section, wherein the rear section is configured to transmit vibrations generated by the electric motor to the body and wherein fasteners are included for fastening the vibrator to an article of clothing by way of a clamping mechanism, the fasteners being removably attached to the fastening section of the housing and being flush with the front section, the housing including a head part and adjacent to the head part a connecting element for charging of the power source, the head part being foldable to allow the connecting element to be exposed after folding.

2. The vibrator of claim 1 wherein the fasteners are configured magnetically.

3. The vibrator of claim 2 wherein the fasteners comprise a fastening plate of magnetic material and at least one magnet arranged on the fastening section.

4. The vibrator of claim 1 wherein the rear section comprises a projection which is configured as a vibratory part for the stimulation of body parts.

5. The vibrator of claim 1 wherein the surface transition between the front section of the housing and the fastening means is essentially smooth.

6. The vibrator of claim 1 wherein the transition between the head part and the rear section is formed by a flexible section.

7. The vibrator of claim 6 wherein the head part is foldable by essentially 180° around the flexible section, which acts as the axis of a hinge.

8. The vibrator of claim 1 wherein the connecting element is configured as a USB type A plug, which is adapted to electrical connection with a USB type A port.

9. The vibrator of claim 6 wherein, after the head part has been folded over by 180° and the fastening plate has been removed, the connecting element is exposed.

10. The vibrator of claim 3 wherein with the exception of the fastening plate, the external elements of the housing comprise silicone material.

11. The vibrator of claim 1 wherein the communications device comprises a Bluetooth module, which is adapted to wireless communication in both directions.

12. The vibrator of claim 1 comprising a plurality of preferably miniaturized vibratory motors, which are adapted to the transmission of vibrations from the vibrator to the body.

* * * * *